(12) United States Patent
O'Connell et al.

(10) Patent No.: US 10,688,277 B2
(45) Date of Patent: Jun. 23, 2020

(54) GUIDE EXTENSION CATHETER WITH PERFUSION OPENINGS

(71) Applicant: Medtronic Vascular, Inc., Santa Rosa, CA (US)

(72) Inventors: Barry O'Connell, Galway (IE); Michael Morrissey, Galway (IE); Sean Ward, Dublin (IE); John Tuohy, Glare (IE); Michael Donegan, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 785 days.

(21) Appl. No.: 15/273,749

(22) Filed: Sep. 23, 2016

(65) Prior Publication Data

US 2017/0080178 A1 Mar. 23, 2017
US 2019/0151607 A9 May 23, 2019

Related U.S. Application Data

(60) Provisional application No. 62/222,556, filed on Sep. 23, 2015.

(51) Int. Cl.
*A61M 25/00* (2006.01)
*A61M 25/06* (2006.01)
*A61M 25/01* (2006.01)

(52) U.S. Cl.
CPC ........ *A61M 25/005* (2013.01); *A61M 25/007* (2013.01); *A61M 25/0045* (2013.01);
(Continued)

(58) Field of Classification Search
CPC .. A61M 2025/0057; A61M 2025/0175; A61M 25/0045; A61M 25/005;
(Continued)

(56) References Cited

U.S. PATENT DOCUMENTS 4,976,691 A 12/1990 Sahota
5,290,247 A 3/1994 Crittenden
(Continued)

FOREIGN PATENT DOCUMENTS

CN 102510763 6/2012
CN 203208504 9/2013
(Continued)

OTHER PUBLICATIONS

Brochure, Boston Scientific Guidezilla, Guide Extension Catheter, 2014.
(Continued)

*Primary Examiner* — Jason E Flick
(74) *Attorney, Agent, or Firm* — Shumaker & Sieffert, P.A.

(57) ABSTRACT

A guide extension catheter includes a proximal shaft, a distal shaft, and a plurality of perfusion openings. The distal shaft includes a jacket and a helical coil structure embedded in the jacket, the distal shaft defining a lumen. The plurality of perfusion openings are disposed though the jacket of the distal shaft between windings of the helical coil structure. The guide extension catheter provides additional back support to the guide catheter. The plurality of perfusion openings allow fluid communication between an area outside the guide extension catheter and the lumen.

23 Claims, 13 Drawing Sheets

(52) U.S. Cl.
CPC ........ *A61M 25/01* (2013.01); *A61M 25/0662* (2013.01); *A61M 2025/0004* (2013.01); *A61M 2025/0057* (2013.01); *A61M 2025/0073* (2013.01); *A61M 2025/0175* (2013.01); *A61M 2025/0681* (2013.01)

(58) Field of Classification Search
CPC .. A61M 25/01; A61M 25/00; A61M 25/0021; A61M 25/0043; A61M 2025/0046; A61M 25/0052; A61M 25/0053; A61M 25/0054; A61M 2025/0059; A61M 2025/0062; A61M 25/0067; A61M 25/008; A61M 25/0068; A61M 25/007
USPC .......................................................... 604/527
See application file for complete search history.

(56) References Cited

U.S. PATENT DOCUMENTS

| | | | |
|---|---|---|---|
| 5,462,523 | A | 10/1995 | Samson et al. |
| 5,527,292 | A | 6/1996 | Adams et al. |
| 5,569,197 | A * | 10/1996 | Helmus ............... A61M 25/09 604/102.02 |
| 5,776,141 | A | 7/1998 | Klein et al. |
| 5,782,811 | A * | 7/1998 | Samson ............... A61M 25/005 604/527 |
| 5,980,486 | A | 11/1999 | Enger |
| 5,997,487 | A | 12/1999 | Kolehmainen et al. |
| 6,638,268 | B2 | 10/2003 | Niazi |
| 7,232,452 | B2 | 6/2007 | Adams et al. |
| 7,316,678 | B2 | 1/2008 | Nash et al. |
| 7,717,899 | B2 | 5/2010 | Bowe et al. |
| 7,972,294 | B2 | 7/2011 | Nash et al. |
| 8,048,032 | B2 | 11/2011 | Root et al. |
| 8,118,803 | B1 | 2/2012 | Chow |
| 8,251,978 | B2 | 8/2012 | Nash et al. |
| 8,292,850 | B2 | 10/2012 | Root et al. |
| 8,753,312 | B2 | 6/2014 | Bowe et al. |
| 8,764,724 | B2 | 7/2014 | Itou et al. |
| 8,939,960 | B2 | 1/2015 | Rosenman et al. |
| RE45,380 | E | 2/2015 | Root et al. |
| 8,996,095 | B2 | 3/2015 | Anderson et al. |
| 9,144,662 | B2 | 9/2015 | Di Caprio et al. |
| RE45,760 | E | 10/2015 | Root et al. |
| RE45,776 | E | 10/2015 | Root et al. |
| 9,352,123 | B2 | 5/2016 | Zhou et al. |
| 2003/0195546 | A1 | 10/2003 | Solar et al. |
| 2007/0149927 | A1 | 6/2007 | Itou et al. |
| 2010/0114062 | A1* | 5/2010 | Wilson ............... A61M 25/005 604/508 |
| 2011/0251519 | A1* | 10/2011 | Romoscanu ...... A61M 25/0013 600/585 |
| 2012/0150271 | A1 | 6/2012 | Fischell et al. |
| 2013/0116701 | A1 | 5/2013 | Wang et al. |
| 2013/0237962 | A1 | 9/2013 | Kawai |
| 2014/0012281 | A1 | 1/2014 | Wang et al. |
| 2014/0018773 | A1 | 1/2014 | Wang et al. |
| 2014/0025004 | A1 | 1/2014 | Falk et al. |
| 2014/0025043 | A1 | 1/2014 | Wang et al. |
| 2014/0039461 | A1 | 2/2014 | Anderson et al. |
| 2014/0052097 | A1 | 2/2014 | Petersen et al. |
| 2014/0249508 | A1 | 9/2014 | Wang et al. |
| 2014/0276618 | A1* | 9/2014 | Di Caprio ......... A61M 25/0068 604/510 |
| 2015/0151090 | A1 | 6/2015 | Sutton et al. |
| 2015/0190617 | A1 | 7/2015 | Anderson et al. |
| 2015/0246209 | A1 | 9/2015 | Holzer |
| 2016/0121080 | A1 | 5/2016 | Cottone |

FOREIGN PATENT DOCUMENTS

| | | |
|---|---|---|
| CN | 203263993 | 11/2013 |
| CN | 104185490 | 12/2014 |
| CN | 104602718 | 5/2015 |
| CN | 104768603 | 7/2015 |
| CN | 104812420 | 7/2015 |
| CN | 104902950 | 9/2015 |
| CN | 105163789 | 12/2015 |
| EP | 0537985 | 3/1997 |
| EP | 0810003 A2 | 12/1997 |
| JP | 2015509030 | 3/2015 |
| JP | 5770105 | 8/2015 |
| JP | 2015523186 | 8/2015 |
| JP | 2015524737 | 8/2015 |
| JP | 2015525636 | 9/2015 |
| JP | 2015525638 | 9/2015 |
| JP | 2015526159 | 9/2015 |
| JP | 2015526160 | 9/2015 |
| JP | 2016517320 | 6/2016 |
| WO | WO2013/070758 | 5/2013 |
| WO | WO2013/116521 | 8/2013 |
| WO | WO2014/011677 | 1/2014 |
| WO | WO2014/012049 | 1/2014 |
| WO | WO2014/015308 | 1/2014 |
| WO | WO2014015062 | 1/2014 |
| WO | WO2014/022310 | 2/2014 |
| WO | WO2014/028898 | 2/2014 |
| WO | WO2014/037836 | 3/2014 |
| WO | WO2014/043694 | 3/2014 |
| WO | WO2014/133897 | 9/2014 |
| WO | WO2014/152191 | 9/2014 |

OTHER PUBLICATIONS

Brochure, Vascular Solution, Inc., GuideLiner V3, 2013.
PCT/US2016/053253, The International Search Report and the Written Opinion of the International Searching Authority, dated Dec. 5, 2016.
Communication Pursuant to Rules 161(1) and 162 EPC dated May 3, 2018, from counterpart European Application No. 16774815.1, 3 pp.
Response to Communication pursuant to 161(1) and 162 EPC dated May 3, 2018, from counterpart European Application No. 16774815.1, filed Nov. 5, 2018, 22 pp.
First Office Action, and English translation thereof, from counterpart Chinese Application No. 201680054973.0, dated Mar. 20, 2020, 27 pp.

* cited by examiner

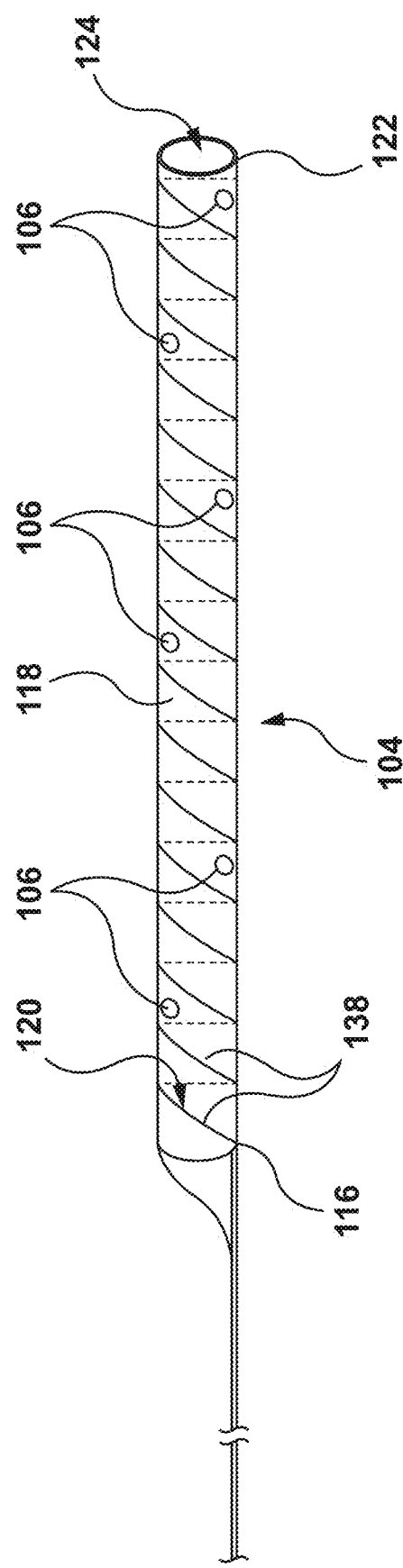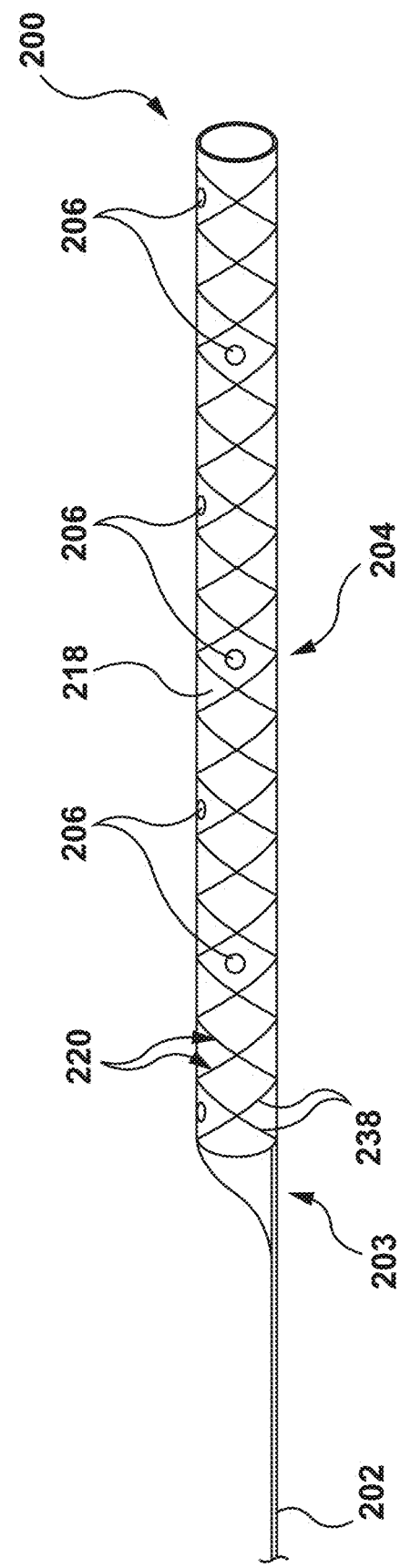
FIG. 4
FIG. 5

Perfusion Prototype
Porcine LAD 1st Diag

GUIDE EXTENSION CATHETER WITH PERFUSION OPENINGS

CROSS-REFERENCE TO RELATED APPLICATIONS

This application claims the benefit under 35 U.S.C. § 119(e) of the filing date of U.S. Provisional Application No. 62/222,556 filed Sep. 23, 2015.

FIELD OF THE INVENTION

The present invention relates to a guide extension catheter for use with a guide catheter. More particularly, the present invention relates to a guide extension catheter with perfusion openings for providing blood flow distal of the guide extension catheter and reducing dampening of the blood pressure wave in the guide catheter.

BACKGROUND

Arteries of the heart, and more specifically coronary arteries, may sometimes be occluded or narrowed by atherosclerotic plaques or other lesions. These afflictions are generally referred to as coronary heart disease or a stenosis, and result in inadequate blood flow to distal arteries and tissue. Heart bypass surgery may be a viable surgical procedure for certain patients suffering from coronary heart disease. However, attendant with traditional open surgery, significant patient trauma, discomfort, extensive recuperation times, and life threatening complications may occur due the invasive nature of the surgery and the necessity for stoppage of the heart during such a surgery.

To address these concerns, efforts have been made to perform interventional cardiology procedures using minimally invasive techniques. In certain efforts, percutaneous transcatheter (or transluminal) delivery and implantation of interventional coronary devices are employed to solve the problems presented by traditional open surgery. Typically, a guide catheter is first inserted through an incision into a femoral (transfemoral), or radial (transradial) artery of a patient. Transradial access is increasingly accepted as a method offering lower post-operative bleeding complications and quicker recovery times for patients. However the smaller diameter of the radial artery requires a smaller diameter guide catheter. The smaller diameter guide catheter has less back support than a similarly configured femoral guide catheter. For example, the Seldinger technique may be utilized in either method for percutaneously introducing the guide catheter. In such methods, the guide catheter is advanced through the aorta and inserted into the opening of an ostium of a coronary artery. A guidewire, or other interventional devices, such as a stent or balloon may be introduced through the guide catheter and maneuvered/advanced through the vasculature and the stenosis of the diseased coronary artery. However, when attempting to pass through a difficult stenosis, or when conducting a radial intervention using a small diameter guide catheter, the guide catheter may not have adequate back support, and continued application of force to advance the interventional device though the stenosis may cause the distal end of the guide catheter to dislodge from the opening of the ostium of the coronary artery, resulting in potential damage to the surrounding tissue.

In order to prevent the guide catheter from dislodging, interventional cardiologists sometimes would deep seat the guide catheter into the coronary artery. The term "deep seat" or "deep seating" means that guide catheter would be pushed farther downstream into the coronary artery. However, deep seating the guide catheter risks the guide catheter damaging the coronary artery wall (dissection or rupture), occluding the coronary artery, and interfering with blood flow to the coronary artery.

One attempt to provide additional back support to a guide catheter that has gained acceptance is the use of a guide extension catheter. The guide extension catheter is deployed within a lumen of the guide catheter and extends distally from the distal end of the guide catheter into the coronary artery. Their smaller size (compared to the guide catheter) allows the guide extension catheter to be seated more deeply in the coronary artery with less potential damage. This provides additional back support to the guide catheter to aid in delivery of interventional devices. In cases with a difficult stenosis or radial interventions, the use of the guide extension catheter reduces the risk of dislodging the guide catheter from the opening of the ostium of the coronary artery during treatment.

Because conventional guide extension catheters are used to provide support for guide catheters, such guide extension catheters must be structurally sound. Thus, distal portions of such guide extension catheters conventionally include a wire support or braid, as described in more detail below, to provide strength to the guide extension catheter. It is not desirable to weaken such guide extension catheters. Conventional guide extension catheters are also designed to be smooth such that they can be advanced through tortuous and calcified arteries. Thus, it is not desirable to increase friction of conventional guide extension catheters. Contrast solution is sometimes injected through the guide catheter and guide extension catheter into the coronary artery. It is not desirable for such contrast solution to be lost into the aorta instead of injected into the coronary artery.

Further, even with its smaller size, when deep-seated, the guide extension catheter may occlude the coronary artery. This will interfere with blood flow through the coronary artery and dampen the AO pressure wave measured proximally down the guide catheter.

In particular, during a procedure, the guide catheter fills with blood. A pressure sensor is disposed outside the body and measures blood pressure at the distal end of the guide catheter through the fluid column which fills the guide catheter. Thus, changes in blood pressure at the distal end of the guide catheter propagate through the guide catheter and are measured by the pressure sensor at the proximal end of the guide catheter. However, using a guide extension catheter deep seated in the coronary artery may interfere with blood flow at the coronary artery. Such interference affects the blood pressure measurement at the proximal end of the guide catheter. Specifically, the blood pressure wave is dampened. As explained in more detail below, the measured systolic pressure and measured diastolic pressure both decrease. Further, both decrease such that the normal blood pressure wave flattens or dampens such that it is less like a wave and more like a flat line. This dampened blood pressure wave indicates that blood flow at the distal end of the guide extension catheter has been disrupted. This dampened blood pressure wave also indicates that blood flow to arteries distal of the guide extension catheter has been disrupted, (i.e. reduced) which endangers the patient.

Due to the risks described above, use of a guide extension catheter may result in a sense of urgency on the part of the interventional cardiologist to complete the procedure quickly, which can result in additional complications.

In order to avoid some of these complications, instructions for use of conventional guide extension catheters instruct that the guide extension catheter is to be inserted into vessels significantly larger than the guide extension catheter. For example, instructions for use for a conventional 6 French guide extension catheter (outer diameter of approximately 1.75 mm) states that the product is not to be inserted into arteries with a diameter of less than 2.5 mm.

However, in use and despite the instructions for use, the complications described above persist. Accordingly, there exists a need for an improved guide extension catheter design that provides the needed additional back support to the guide catheter and reduces dampening of the AO pressure wave within the guide catheter, while minimizing the potential to occlude the coronary artery.

SUMMARY OF THE INVENTION

Embodiments hereof relate to a guide extension catheter including a proximal shaft, a distal shaft, and a plurality of perfusion openings. The distal shaft includes a jacket and a helical coil structure embedded in the jacket, the distal jacket defining a lumen. The plurality of perfusion openings are disposed through the jacket of the distal shaft between windings of the helical coil structure. The guide extension catheter is configured to extend through a guide catheter and provide additional back support to the guide catheter. The plurality of perfusion openings are configured to allow fluid communication between an area outside the guide extension catheter and the lumen of the guide extension catheter.

Embodiments hereof also relate to a guide extension catheter including a proximal shaft, a distal shaft, and a plurality of perfusion openings. The distal shaft includes a jacket and a braided structure embedded in the jacket, the distal shaft defining a lumen. The braided structure includes a plurality of wire members woven together to form the braided structure. The plurality of perfusion openings are disposed through the jacket of the distal shaft between the wire members of the braided structure. The guide extension catheter is configured to extend through a guide catheter and provide additional back support to the guide catheter. The plurality of perfusion openings is configured to allow fluid communication between an area outside the guide extension catheter and the lumen of the guide extension catheter.

Embodiments hereof also relate to a guide extension catheter including a proximal shaft and a distal shaft. The distal shaft includes a braided jacket including a plurality of woven wire members, the distal shaft defining a lumen. The plurality of wire members are woven together such that a plurality of perfusion openings are formed between the wire members, wherein the plurality of perfusion openings extend from an outer surface of the distal shaft to a lumen of the distal shaft. The guide extension catheter is configured to extend through a guide catheter and provide additional back support to the guide catheter. The plurality of perfusion openings are configured to allow fluid communication between an area outside the guide extension catheter and the lumen of the guide extension catheter.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 4 is a perspective illustration of the distal shaft of the guide extension catheter of FIG. 1.

FIG. 5 is a perspective illustration of a portion of a guide extension catheter in accordance with another embodiment hereof.

DETAILED DESCRIPTION

Specific embodiments of the present invention are now described with reference to the figures, wherein like reference numbers indicate identical or functionally similar elements. The terms "distal" and "proximal", when used in the following description to refer to a guidewire, catheter, and/or other system component hereof are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a native vessel or native valve are used with reference to the direction of blood flow from the heart. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Furthermore, there is no intention to be bound by any expressed or implied theory presented in the preceding technical field, background, brief summary, or the following detailed description.

Figure 1:
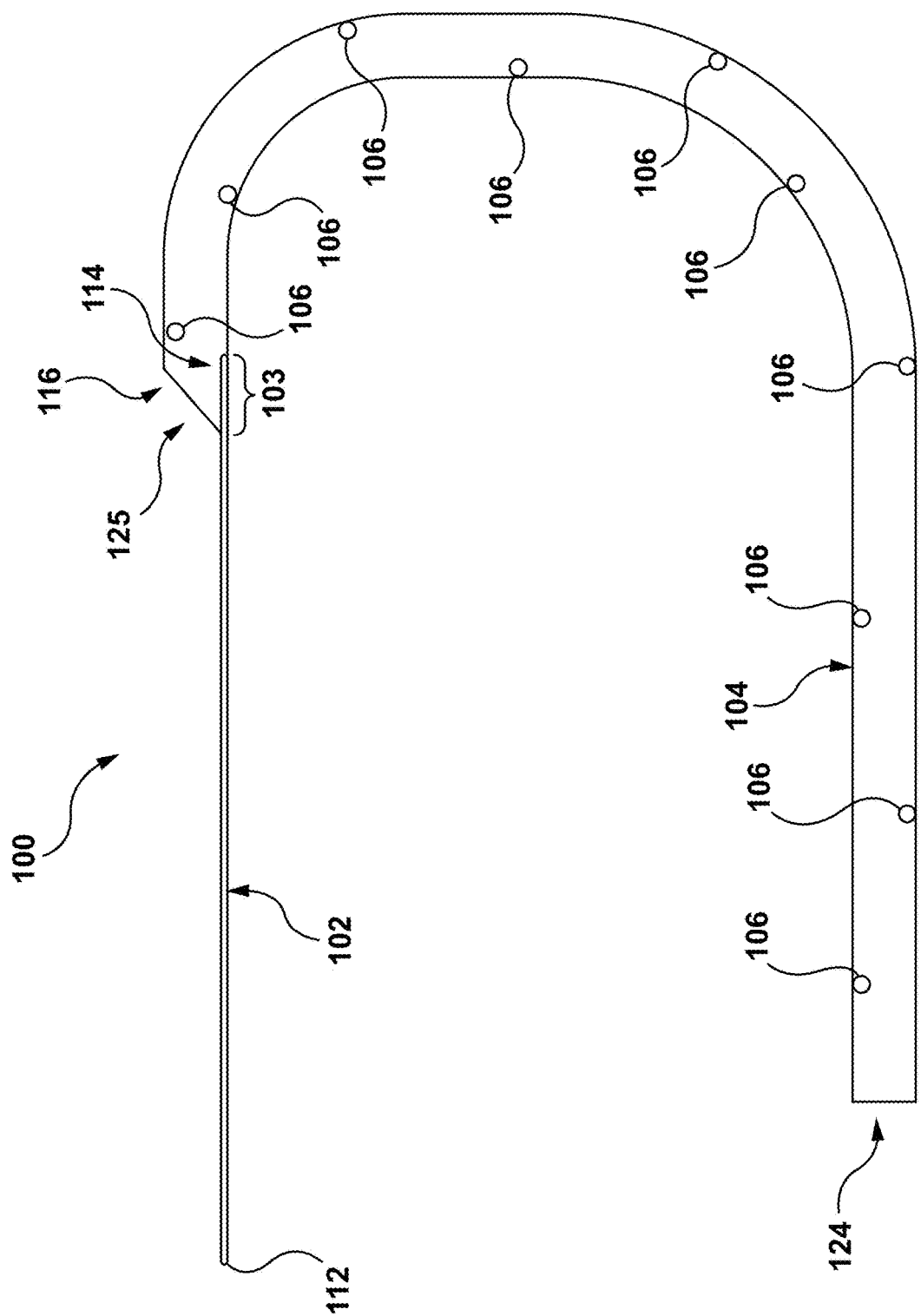
FIG. 1 is a side view illustration of a guide extension catheter in accordance with an embodiment hereof.
Figure 2:
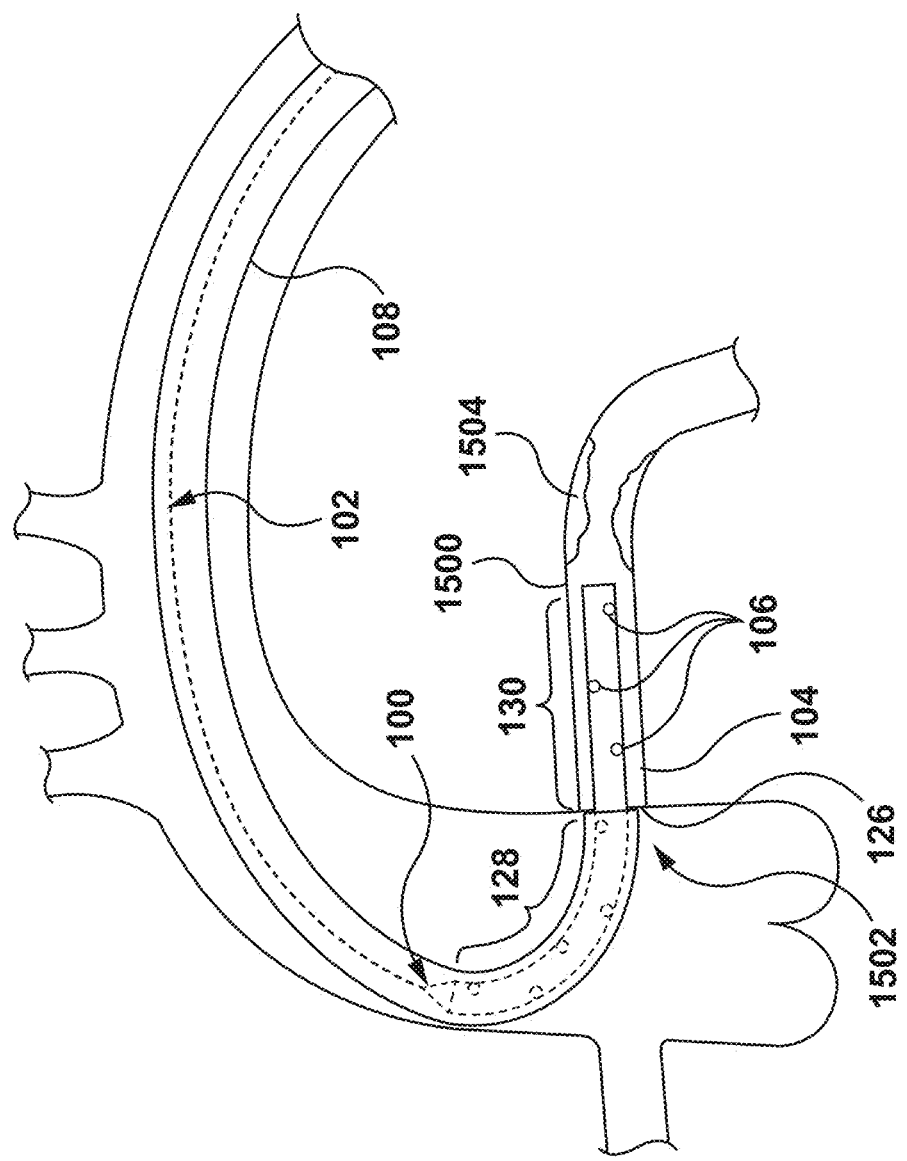
FIG. 2 is a side view illustration of the guide extension catheter of FIG. 1 extending through a guide catheter and disposed within a coronary artery.

FIGS. 1-5 illustrate a guide extension catheter 100 in accordance with an embodiment hereof. The guide extension catheter 100, as shown in FIG. 1, includes a proximal shaft 102 and a distal shaft 104 coupled to each other at a transition joint 103. The distal shaft 104 includes a plurality of perfusion openings 106, as described in greater detail below. The guide extension catheter 100 is configured for advancement through a guide catheter 108, as shown in FIG. 2. The guide extension catheter 108 is further configured to be seated within a coronary artery 1500 such that the guide extension catheter 100 provides additional back support to the guide catheter 108. The guide extension catheter 100 is further configured such that the plurality of perfusion openings 106 provide blood flow to the coronary artery 1500 and permit blood flow into the lumen of the guide extension catheter such that blood pressure propagates through the fluid column of the guide catheter 108 for the AO blood pressure measurements. In an embodiment, the guide extension catheter 100 may be between 20 cm and 40 cm in length, with 4 cm-6 cm disposed within the coronary artery 1500, but this is not meant to limit the design and a longer or shorter guide extension catheter 100 may be utilized.

The proximal shaft 102, which may also be referred to as a push member, may be a wire, hypotube, shaft, partial shaft, or any other configuration as would be apparent to those skilled in the art. The proximal shaft 102 includes a proximal end 112 and a distal end 114, as shown in FIG. 1. The distal end 114 of the proximal shaft 102 is coupled to a proximal end 116 of the distal shaft 104 at the transition joint 103. The proximal shaft 102 is configured to transfer motion applied at the proximal end 112 to the distal end 114. The proximal shaft is further configured to transfer motion of the distal end 114 to the transition joint 103. The proximal shaft 102 may be formed of materials such as, but not limited to stainless steel, Nitinol, or other materials suitable for the purposes disclosed herein.

In an embodiment, the transition joint 103 is the proximal portion of the distal shaft 104. In an embodiment, the transition joint is formed by overlapping the distal end 114 of the proximal shaft 102 and the proximal end 116 of the distal shaft 104, as shown in FIG. 1. In other embodiments, the transition joint 103 may be formed of different materials than the distal shaft 104. In some embodiments, the transition joint 103 may be stiffer than the distal shaft 104. For example, and not by way of limitation, the transition joint 103 may be a stainless steel tube embedded between an inner liner 121 and an outer jacket 118, as described in more detail below regarding the distal shaft 104. The transition joint 103 defines a lumen 125, therethrough. The transition joint 103 is configured to couple the proximal shaft 102 to the distal shaft 104 such that motion of the proximal shaft 102 is transferred to the distal shaft 104. The transition joint 103 may also transition from the stiff proximal shaft 102 to the more flexible distal shaft 104.

Figure 3:
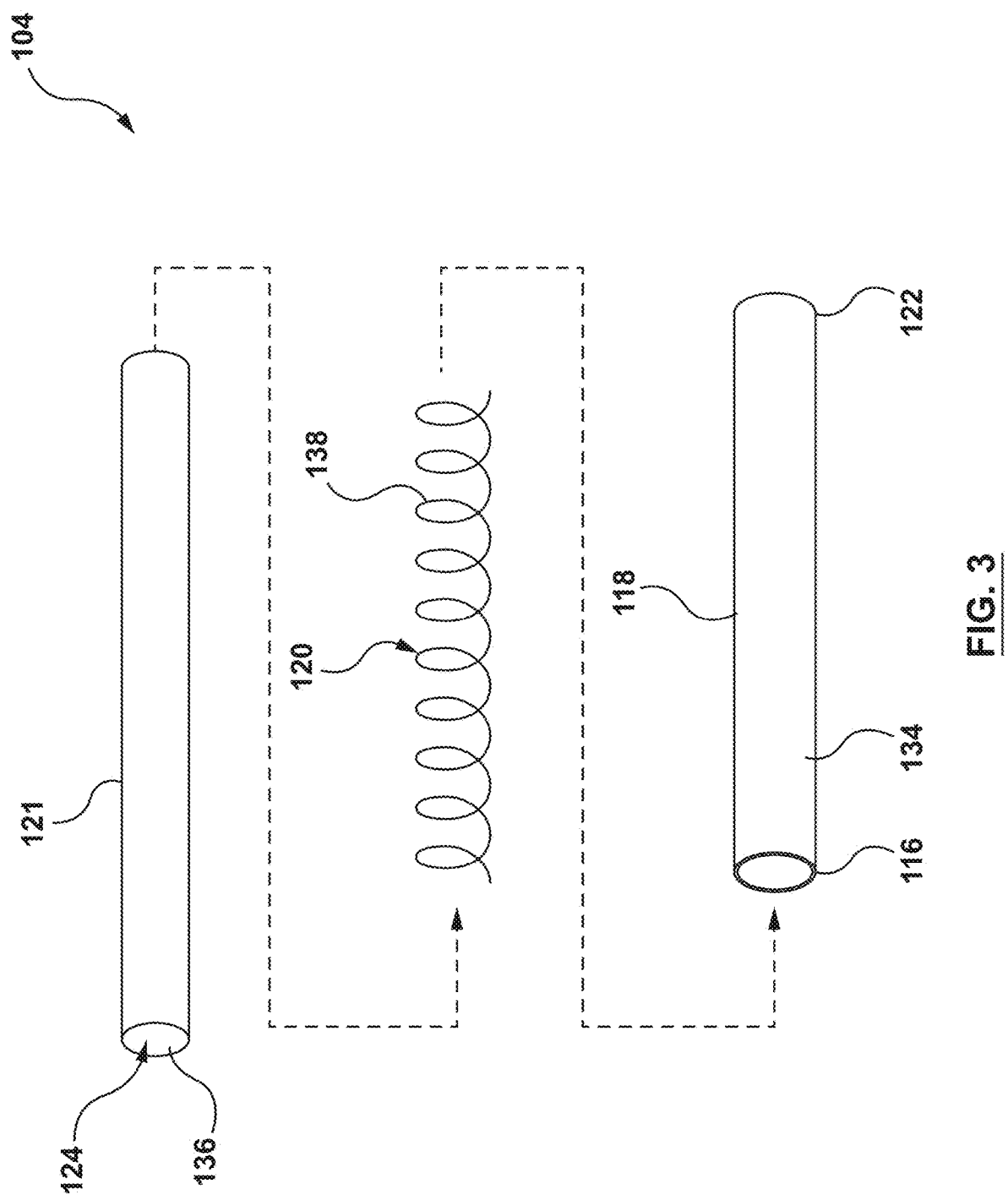
FIG. 3 is an exploded perspective illustration of an embodiment of a distal shaft of the guide extension catheter of FIG. 1.

In an embodiment, the distal shaft 104 includes an inner liner 121, an outer jacket 118 and a helical coil structure 120 embedded therebetween, as shown in of FIG. 3. The distal shaft 104 further includes the plurality of perfusion openings 106, as shown in FIG. 4. The distal shaft 104 further includes the proximal end 116 and a distal end 122, and defines a lumen 124 therethrough, as shown in FIGS. 3-4.

In an embodiment, the inner liner 121 of the distal shaft 104 is of a generally tubular shape and forms an inner surface 136 of the distal shaft 104, as shown in FIG. 3. The inner liner 121 is configured to provide the distal shaft 104 with a low friction inner surface such that interventional devices may be advanced/retracted easily through the lumen 124. The inner liner 121 may be formed from materials such as, but not limited to polytetrafuoroethylene (PTFE), perfluoroalkoxy alkanes (PFAs), high-density polyethylene (HDPA), or other materials suitable for the purposes described herein.

In an embodiment, the outer jacket 118 of the distal shaft 104 is of a generally tubular shape and forms an outer surface 134 of distal shaft 104, as shown in FIG. 3. The outer jacket 118 is configured to provide flexibility to the distal shaft 104. The outer jacket 118 may be formed from materials such as, but not limited to, thermoplastic elastomers, such as but not limited to polyether block amides (e.g. PEBAX®, VESTAMID®), nylon, or other materials suitable for the purposes described herein.

The helical coil structure 120 of the distal shaft 104 is a generally tubular helically wound wire member 138 (also known as a filament). In an embodiment, the helical coil structure 120 is embedded between the inner liner 121 and the outer jacket 118, as shown in FIG. 3. The helical coil structure 120 is configured to provide strength and rigidity to the distal shaft 104. The helical coil structure 120 may be bonded between the inner liner 121 and the outer jacket 118 by methods such as, but not limited to heat, fusion, adhesives, or other methods suitable for the purposes described herein. While the distal shaft 104 of FIGS. 3-4 shows the helical coil structure 120 with only one (1) wire member 138, this is not meant to limit the design, and more than one (1) wire member 138 may be utilized. Moreover, the wire member(s) 138 may be wound (coiled) in differing patterns. The helical coil structure 120 may be formed from materials such as, but not limited to, stainless steel, Nitinol, or other materials suitable for the purposes described herein.

Figure 2A:
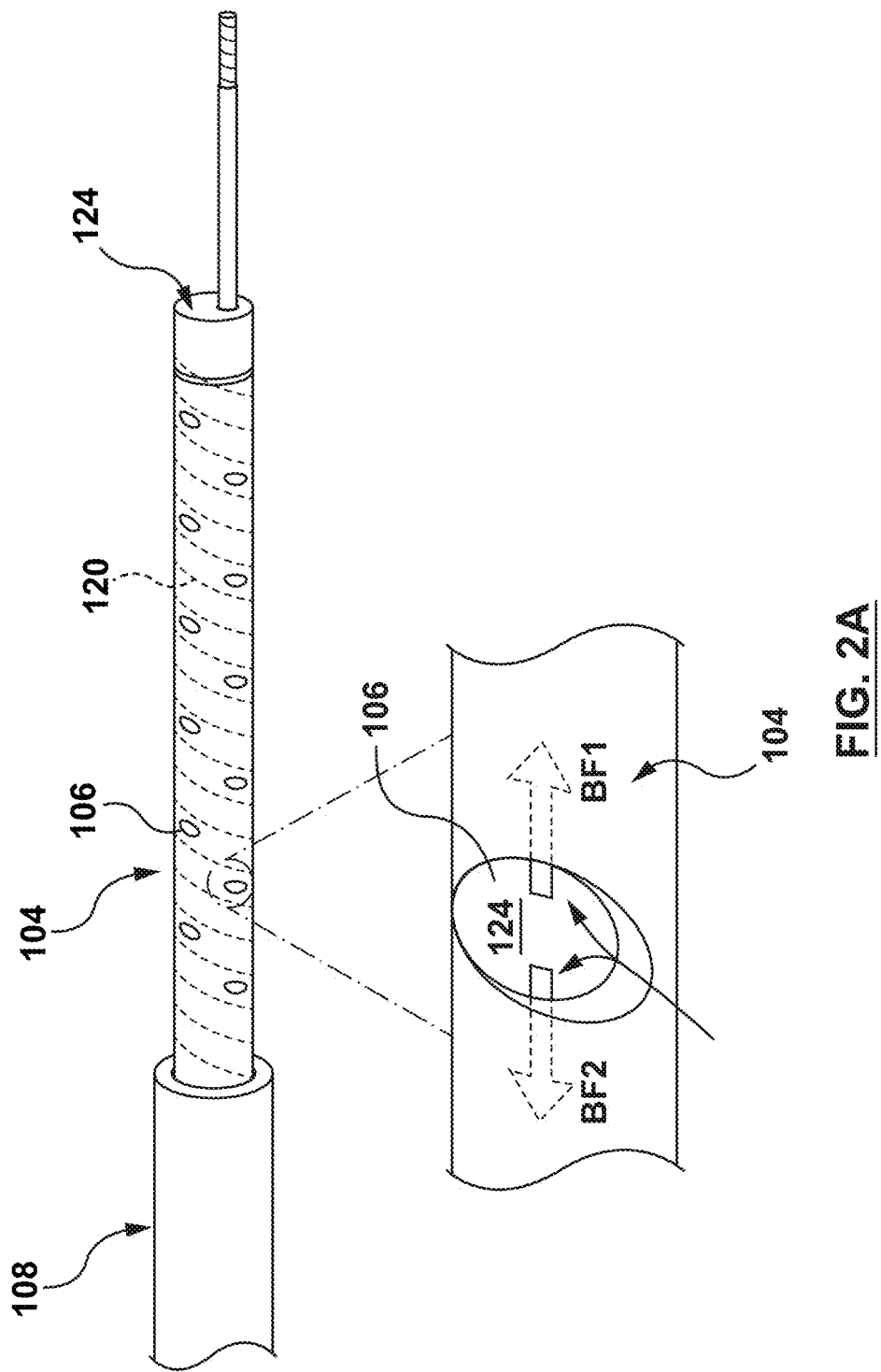
FIG. 2A is an illustration of a distal portion of the guide extension catheter of FIG. 1 extending through a distal portion of a guide catheter.

As described above, the distal shaft 104 of the guide extension catheter 100 includes perfusion openings 106 disposed therethrough. Each perfusion opening 106 is an aperture extending from the outer surface 134 to the inner surface 136 of distal shaft 104. Each perfusion opening 106 is configured to allow fluid flow from/to an area outside the distal shaft 104 to/from the lumen 124 of the distal shaft 104. Each perfusion opening 106 is disposed through the outer jacket 118 and the inner liner 121, between adjacent windings of the helical coil structure 120, as shown in FIGS. 2A and 4. Each perfusion opening 106, so disposed, insures that no sharp edge or wire component of helical coil structure 120 is exposed. The perfusion openings 106 of distal shaft 104 provide blood flow BF1 to the distal vasculature (FIG.

2A). Moreover, the perfusion openings provide blood flow BF2 such that blood pressure at the distal end of the guide catheter 108 is transferred along the fluid column to the pressure sensor at the hub of the guide catheter 108. With adequate distal blood flow provided by the guide extension catheter 100, the interventional cardiologist has more time to complete the procedure with less chance of adverse consequences.

The perfusion openings 106 shown in FIGS. 1-4 may be configured with a shape, such as, but not limited to circles, ellipses, slits, or any other shapes suitable for the purposes described herein. Further, all the perfusions openings 106 do not need to be the same shape or size. Additionally, the perfusion openings 106 may be placed at various locations along the distal shaft 104, as described in greater detail below. Each perfusion opening 106 may be formed by methods such as, but not limited to, laser cutting, mechanical punching, or other methods suitable for the purposes described herein. As described above, the perfusion openings 106 are disposed between windings of the wire member 138 of the helical coil structure 120. In practice, the spaces between the windings of the helical coil structure are very small (the drawings are not to scale). Therefore, the perfusion openings 106 must be formed very precisely in order to avoid the windings of the helical coil structure 120.

As shown in FIG. 2, the guide extension catheter 100 is configured to provide additional back support to the guide catheter 108. A distal end 126 of the guide catheter 108 is disposed within the ostium 1502 of the coronary artery 1500. The distal shaft 104 of the guide extension catheter 100 is disposed with a proximal portion 128 within the guide catheter 108 and a distal portion 130 extending distally from the distal end 126 of the guide catheter 108. The distal portion 130 of the guide extension catheter 100 is seated within the coronary artery 1500. With the guide extension catheter 100 so disposed, the guide extension catheter 100 adds back support to the existing back support of the guide catheter 108. With the additional back support of the guide extension catheter 100, interventional devices, such as stents and guidewires may be passed through the stenosis 1504 without unseating the guide catheter 108 from the ostium 1502 of the coronary artery 1500.

Figure 6:
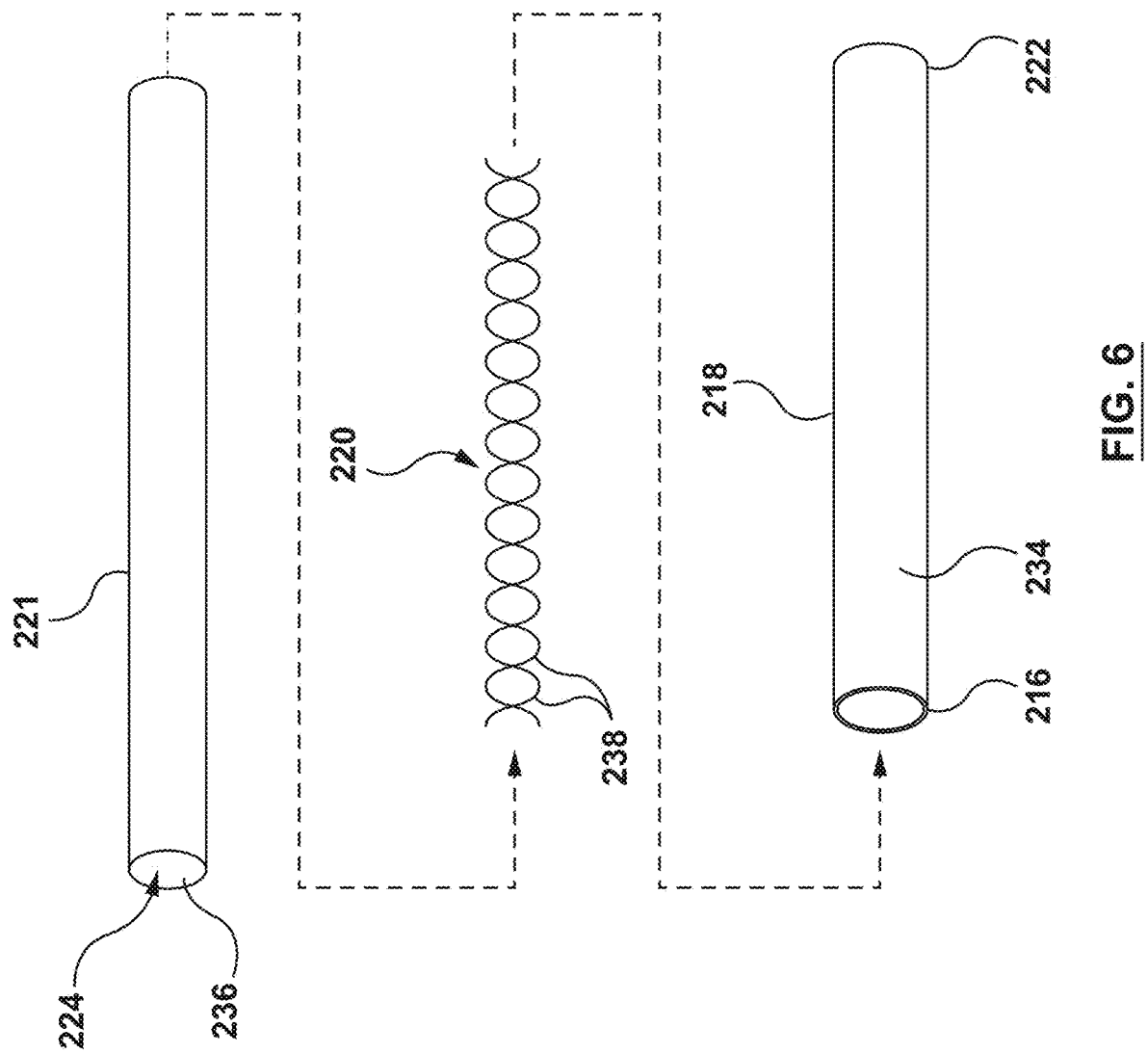
FIG. 6 is an exploded perspective illustration of the distal shaft of the guide extension catheter of FIG. 5.

FIGS. 5-6 show another embodiment of a guide extension catheter 200 including a proximal shaft 202, a distal shaft 204, a transition joint 203 coupling the proximal shaft 202 to the distal shaft 204, and a plurality of perfusion openings 206 disposed through the distal shaft 204. The guide extension catheter 200 is similar to the guide extension catheter 100. Therefore, details of the construction and alternatives will not be repeated. The distal shaft 204 of guide extension catheter 200 is similar to the distal shaft 104 of the guide extension catheter 100. However, instead of the helical coil structure 120, the distal shaft 204 includes a braided structure 220 embedded between an inner liner 221 and an outer jacket 218, as shown in FIG. 6. The inner liner 221 may be similar to the inner liner 121 and the outer jacket 218 may be similar to the outer jacket 118.

The braided structure 220 may be formed by weaving together two continuous wire members 238 in opposite directions in a one-over-one pattern, as shown in FIG. 6. While the distal shaft 204 of FIGS. 5-6 shows braided structure 220 with only two wire members 238, this is not meant to limit the design, and more than two wire members 238 may be utilized. Moreover, while FIG. 6 shows wire members 238 braided in a one-over-one pattern, this is not meant to limit the design, and the wire members 238 may be woven in differing patterns.

The distal shaft 204 includes a plurality of perfusion openings 206. The perfusions openings 206 are similar to the perfusion openings 106 of FIGS. 1-4 and therefore will not be described in detail. As with the perfusion openings 106, the perfusion openings 206 extend from an outer surface 234 of the distal shaft 204 to a lumen 224 of the distal shaft 204. Further, the perfusion openings 206 are formed between the wire members 238 of the braided structure 220.

With the above understanding of examples of guide extension catheters 100, 200, FIGS. 7-16 show various embodiments of the shape, size, and distribution of the plurality of perfusion openings 106, 206. The descriptions of FIGS. 7-16 are made with reference to the distal shaft 104 of FIGS. 1-4 for convenience. The details of the plurality of perfusion openings of each embodiment apply equally to other embodiments disclosed herein. Further, various modifications to the number and specific distribution arrangement of the embodiments of FIGS. 7-16 may be made within the scope of the present invention. Additionally, the sizes, shapes, patterns, and distributions of FIGS. 7-16 may be utilized together in any combination, with the specific configuration optimized for specific treatment purposes.

Figure 7:
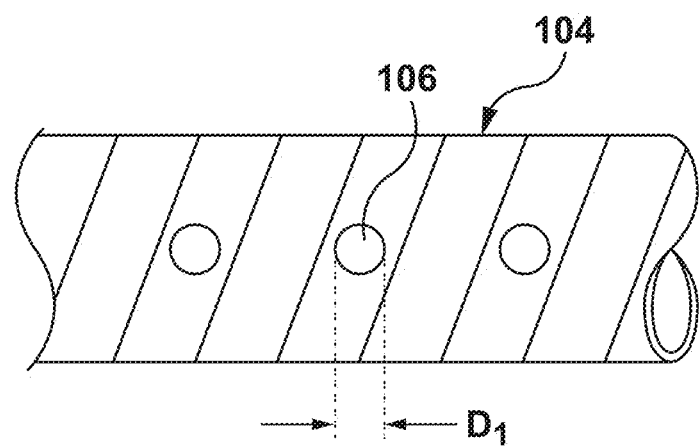
FIG. 7 is a perspective illustration of an embodiment of the perfusion openings of the distal shaft of the guide extension catheter of FIG. 1.

FIG. 7 shows an example of a circular perfusion opening 106. Although only one perfusion opening 106 is shown in FIG. 7, the description below can apply to a plurality of the perfusion openings 106. The perfusion opening 106 of FIG. 7 is circular and has a diameter D1. The diameter D1 may be between 0.01 mm and 0.5 mm such that a 0.014" guidewire cannot pass through any of the perfusion openings 106. This, reduces the potential risk of the guidewire exiting through a perfusion opening 106 and dissecting or otherwise damaging an adjacent artery.

Figure 8:
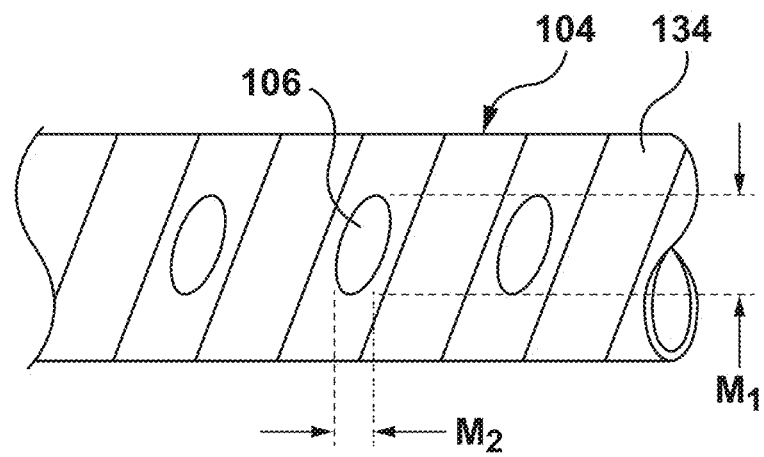
FIG. 8 is a perspective illustration of another embodiment of the perfusion openings of the distal shaft of the guide extension catheter of FIG. 1.

FIG. 8 shows an example of an elliptical perfusion opening 106. Although only one perfusion opening 106 is shown in FIG. 8, the description below can apply to a plurality of the perfusion openings 106. The elliptical perfusion opening 106 has a major axis M1 and a minor axis M2. In an embodiment, the major axis M1 may be between 0.01 mm and 0.5 mm and the minor axis M2 may be between 0.01 mm and 0.5 mm such that a 0.014" guidewire cannot pass through any of the perfusion openings 106. This reduces the potential risk of the guidewire exiting through a perfusion opening 106 and dissecting or otherwise damaging an adjacent artery. The elliptical shape of the perfusion openings 106 of FIG. 8 may optimize flow volume while minimizing the dimension in the longitudinal direction of the distal shaft. Additionally, the elliptical shape may be configured to cover a greater area of the outer surface 134 of the distal shaft 104, thereby capturing a greater volume of blood flow. The elliptical shape also allows the perfusion openings to cover a greater amount of surface area without compromising the helical coil structure 120. Further, while the perfusion opening 106 of FIG. 8 is described as elliptical, it need not be a perfect ellipse. Instead, for example, it can be generally oval in shape.

Figure 9:
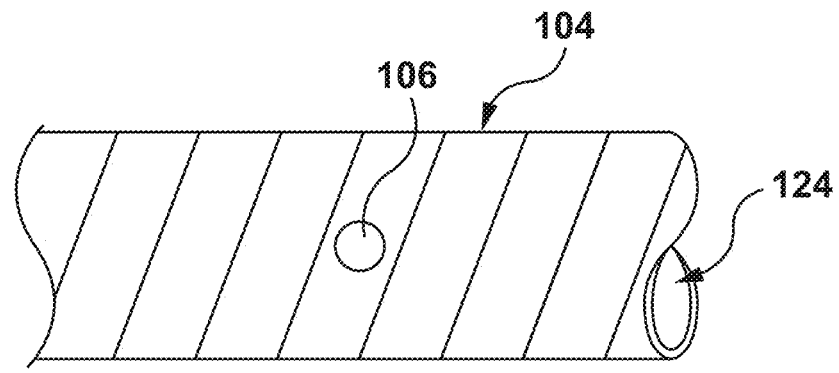
FIG. 9 is a perspective illustration of another embodiment of the perfusion openings of the distal shaft of the guide extension catheter of FIG. 1.

FIG. 9 shows an embodiment with an isolated perfusion opening 106. By an isolated perfusion opening 106, it is meant that the perfusion opening is located at a specific location along the distal shaft 104 for a particular reason. For example, and not by way of limitation, the isolated perfusion opening may be located to provide perfusion to a branch vessel. Accordingly, a plurality of isolated perfusion openings 106 may be provided at specific locations to perfuse different branch vessels. Further, the isolated perfusion openings 106 may be used in combination with other embodiments described herein, wherein the distribution of the perfusion openings 106 serves a different purpose.

Figure 10:
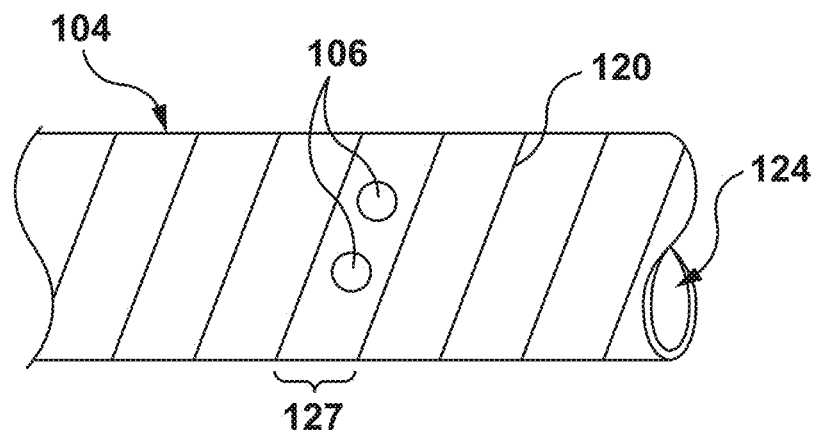
FIG. 10 is a perspective illustration of another embodiment of the perfusion openings of the distal shaft of the guide extension catheter of FIG. 1.

FIG. 10 shows an embodiment with a plurality of the perfusion openings 106 located adjacent to each other in the same space 121 between adjacent windings of the helical coil structure 120. FIG. 10 shows two perfusion openings 106 co-located in the space 127 between adjacent windings of the helical coil structure 120, but more openings 106 can be co-located depending on the space available. Further, FIG. 10 shows only two perfusion openings 106. However, other perfusion openings 106 may be provided along the length of the distal shaft (either co-located or not) in accordance with other embodiments described herein. Locating multiple perfusion openings 106 closely adjacent to each other, as shown in FIG. 10, provides increased blood flow (perfusion) to/from the lumen 124 of the distal shaft 104 at specific locations.

Figure 11:
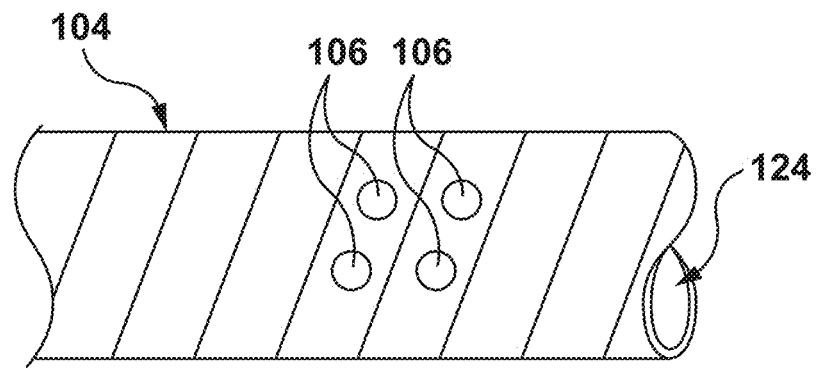
FIG. 11 is a perspective illustration of another embodiment of the perfusion openings of the distal shaft of the guide extension catheter of FIG. 1.

FIG. 11 shows an embodiment with a plurality of the perfusion openings 106 concentrated at a location along the distal shaft 104. In the embodiment shown in FIG. 11, four perfusion openings 106 are concentrated near each other. However, more or fewer perfusion openings 106 may be concentrated at a location near each other. Further, additional perfusion openings 106 may be provided elsewhere along the distal shaft 104, as described in other embodiments. The concentrated distribution of the perfusion openings is configured to provide a bolus of oxygenated blood through the distal shaft 104 to arteries distal of the guide extension catheter 100.

Figure 12:
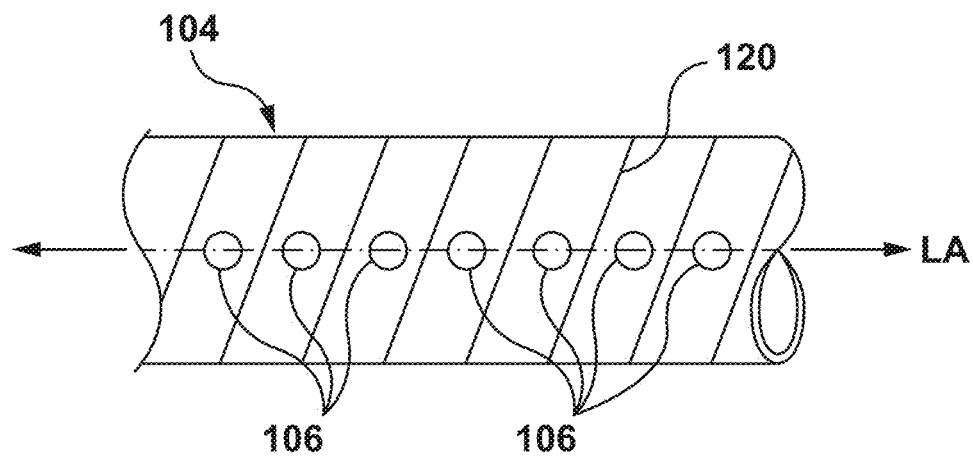
FIG. 12 is a perspective illustration of another embodiment of the perfusion openings of the distal shaft of the guide extension catheter of FIG. 1.
Figure 13:
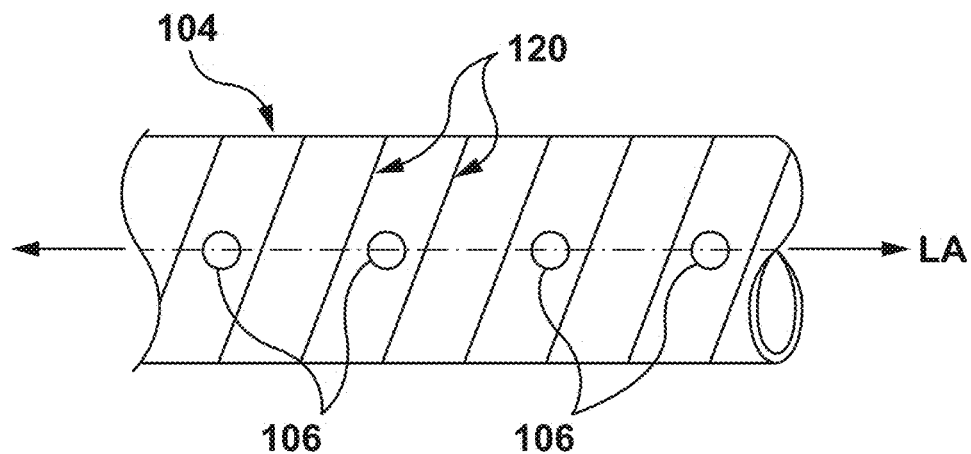
FIG. 13 is a perspective illustration of another embodiment of the perfusion openings of the distal shaft of the guide extension catheter of FIG. 1.

FIG. 12 shows an embodiment with a plurality of the perfusion openings 106 spaced from each other by a single winding of the helical coil structure 120. In the embodiment of FIG. 12, the perfusion openings 106 are also aligned along a common longitudinal axis LA. By providing the plurality of perfusion openings along the longitudinal axis LA, flexibility of the distal shaft 104 is increased in the direction of the plurality of openings 106 as compared to the side of the distal shaft 204 which is opposite the plurality of openings 106. However, the plurality of openings 106 also increases flexibility of the distal shaft 104 in all directions as compared to the same shaft without the plurality of openings. FIG. 13 shows a similar embodiment with the plurality of openings 106 aligned along a common longitudinal axis LA, but with adjacent perfusion openings 106 spaced from each other by two windings of the helical coil structure 120. The alternate-winding spaced distribution of the perfusion openings 106 provides increased flexibility to the distal shaft 104, but the flexibility is less than the embodiment of FIG. 12 due to the alternate-winding spaced distribution.

Figure 14:
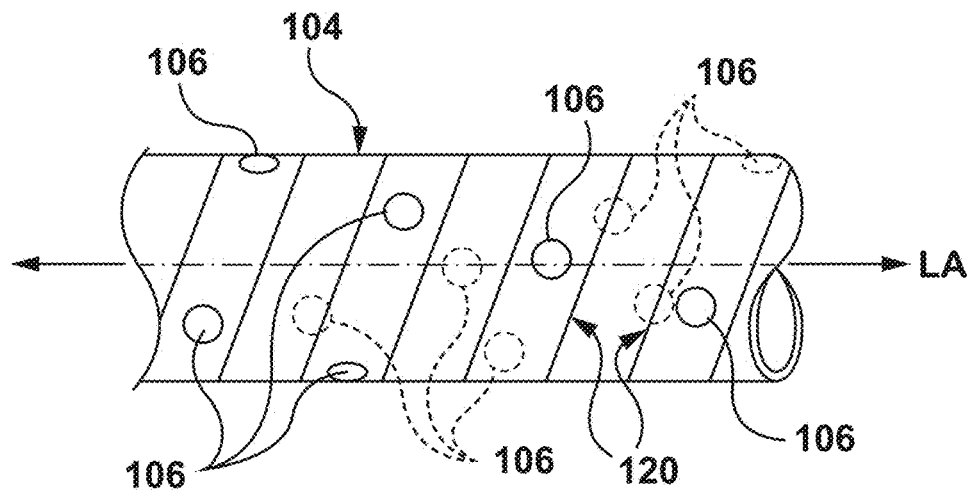
FIG. 14 is a perspective illustration of another embodiment of the perfusion openings of the distal shaft of the guide extension catheter of FIG. 1.

FIG. 14 shows an embodiment with the plurality of perfusion openings 106 arranged spirally around a central longitudinal axis LA of the distal shaft 104. The spiral distribution of the perfusion openings is configured to increase overall flexibility of the distal shaft 104 without biasing the flexibility of the distal shaft 104 in any one direction. The concentration of the perfusion openings 106 along the spiral distribution may be increased or decreased to increase or decrease flexibility of the distal shaft 104.

Figure 15:
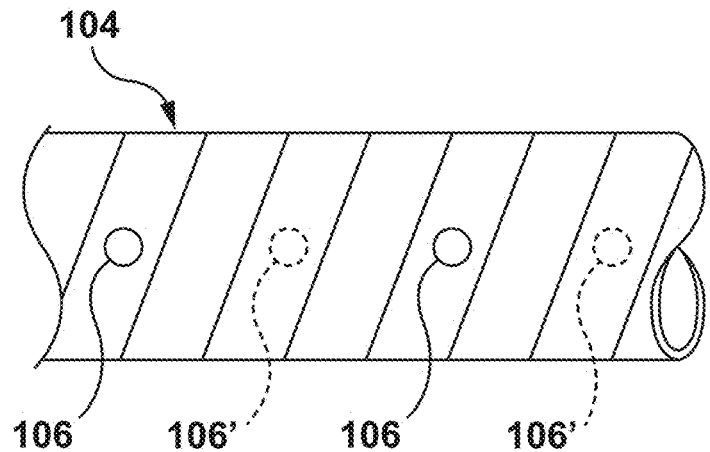
FIG. 15 is a perspective illustration of another embodiment of the perfusion openings of the distal shaft of the guide extension catheter of FIG. 1.

FIG. 15 shows an embodiment with the plurality of perfusion openings 106 disposed on opposing sides of the distal shaft 104. In the embodiment of FIG. 15, the perfusion openings 106 are disposed along a first longitudinal axis (not shown for clarity) and the perfusion openings 106' are disposed along a second longitudinal axis (not shown for clarity) that is spaced 180 degrees from the first longitudinal axis around the circumference of the distal shaft 104. The plurality of perfusion openings 106, 106' generally increase flexibility of the distal shaft. Further, the distribution of the plurality of perfusion openings 106, 106' longitudinally along opposite walls of the distal shaft specifically increases flexibility of the distal shaft 104 in the direction of each wall with the perfusion openings 106, 106' (i.e., into and out of the paper in FIG. 15) as compared to the directions without the perfusion openings (i.e., up a down in FIG. 15).

Figure 16:
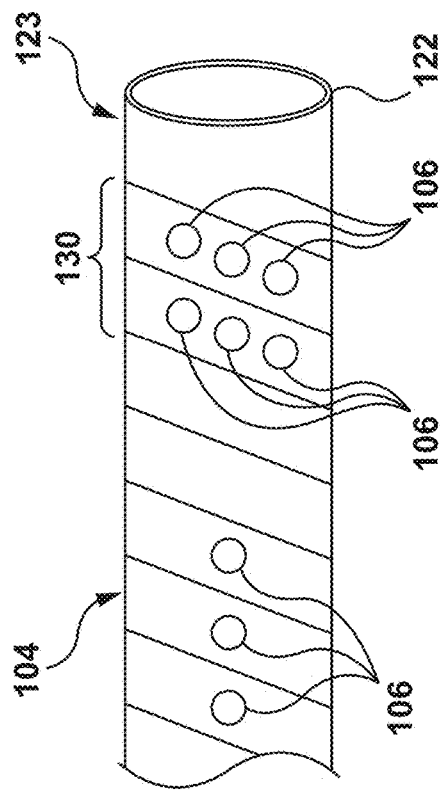
FIG. 16 is a perspective illustration of another embodiment of the perfusion openings of the distal shaft of the guide extension catheter of FIG. 1.

FIG. 16 shows an embodiment with a greater concentration of the plurality of perfusion openings 106 at a distal portion 130 near the distal end 122 of the distal shaft 104 than a proximal portion of the distal shaft 104. By providing more of the perfusion openings 106 at the distal portion 130 of the distal shaft 104, the flexibility of the distal shaft 104 increases at the distal portion 130. Increased flexibility near the distal end 122 provides a softer distal portion 130, increasing deliverability and reducing potential damage to adjacent tissue as the distal shaft 104 is advanced. The embodiment of FIG. 16 shows perfusion openings 106 proximal of the distal portion 130. However, the proximal perfusion openings can be omitted. In other similar embodiments, the concentration of perfusion openings gradually increases from a proximal portion of the distal shaft 104 to a distal portion of the proximal shaft 104, thereby gradually increasing the flexibility of the distal shaft 104 toward the distal portion.

Figure 17:
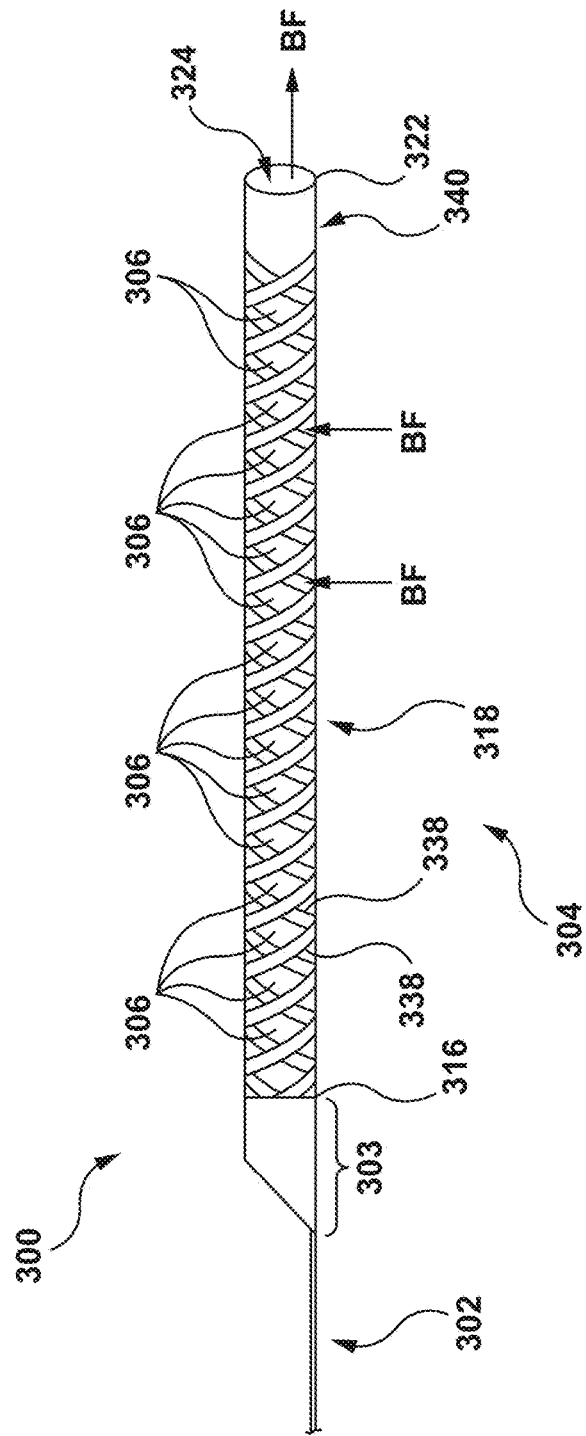
FIG. 17 is a perspective illustration of a portion of a guide extension catheter in accordance with another embodiment hereof.
Figure 18:
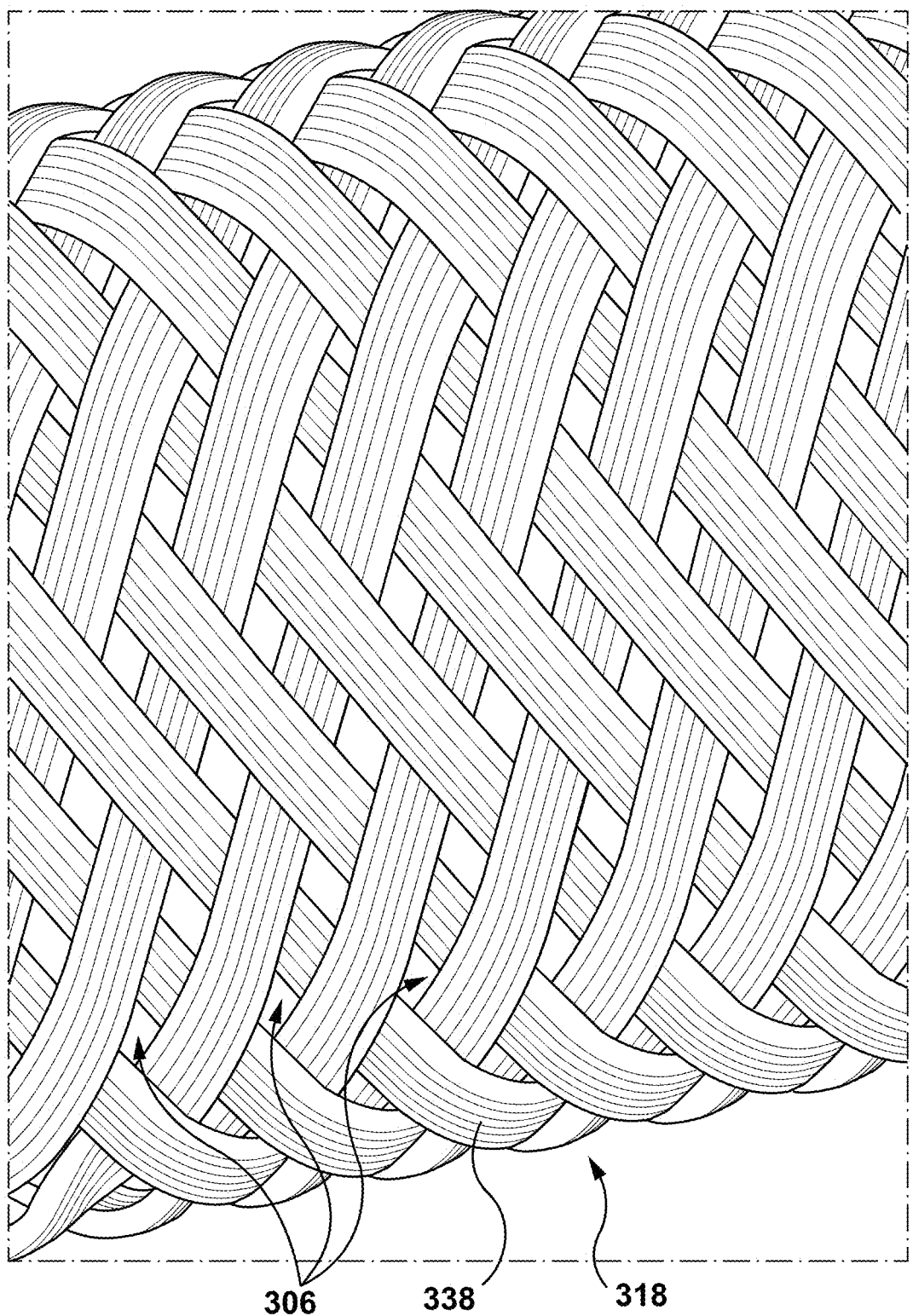
FIG. 18 is a close-up view of a portion of the distal shaft of the guide extension catheter of FIG. 17.

FIGS. 17-18 show another embodiment of a guide extension catheter 300. Guide extension catheter 300 includes a proximal shaft 302, a distal shaft 304, and a transition joint 303 coupling the proximal shaft 302 and the distal shaft 304. The proximal shaft 302 and the transition joint 303 may be similar to the proximal shaft 102 and the transition joint 103 described above, and therefore are not described in detail with respect to FIGS. 17-18.

The distal shaft 304 of the guide extension catheter 300 includes a braided jacket 318 and a distal tip 340, as shown in FIG. 17. The distal shaft 304 further includes a plurality of perfusion openings 306 formed by the braided jacket 318, as described in greater detail below. The distal shaft 304 defines a lumen 324 extending from a proximal end 316 to a distal end 322 of the distal shaft. The guide extension catheter 300 is configured to provide additional back support to a guide catheter (not shown in FIG. 19) similar to the guide extension catheters 100, 200, described previously.

The braided jacket 318 of the distal shaft 304 includes a plurality of wire members 338 woven to form a generally tubular shape, as shown in FIGS. 17-18. The braided jacket 318 is configured to provide flexibility, strength, and rigidity to the distal shaft 304. Moreover, the braided jacket 318 forms the plurality of perfusion openings 306 between the adjacent woven wire members 338. The perfusion openings 306 extend from an outer surface to the lumen 324 of the distal shaft 304. The weave of the braided jacket 318 should be tight enough to maintain structural integrity of the distal shaft 304, but not too tight such that the distal shaft 304 becomes inflexible and/or the adjacent wire members 338 occlude the corresponding perfusion openings 306. The braided jacket 318 is formed by weaving together the plurality of wire members 338 in opposite directions in a one-over-one pattern. The weaving pattern, number and size of the wire members 338 may be varied. The wire members 338 of the braided jacket 318 may be formed from materials such as, but not limited to, stainless steel, Nitinol, or other materials suitable for the purposes described herein.

In an embodiment, the distal shaft 304 includes the distal tip 340, as shown in FIG. 17. The distal tip 340 is disposed at the distal end 322 of the distal shaft 304. The distal tip 340 is configured to provide a soft distal end to the distal shaft 304 such that the distal shaft 1404 does not damage the surrounding tissue as the distal shaft 304 is advanced through the vasculature of the patient. The distal tip 340 may be formed from materials such as, but not limited to, polymers, or other materials suitable for the purposes described herein. The distal tip 340 may be coupled to the braided jacket 318 of the distal shaft 304 in a manner such as, but not limited to adhesives, fusing, welding, or other methods suitable for the purposes disclosed herein.

Each perfusion opening 306 may be defined by the edges of adjacent woven wire members 338 forming the perfusion opening 306. In the embodiment shown in FIGS. 17-18, each perfusion opening 306 is a quadrilateral. Further, each perfusion opening in FIGS. 17-18 is the same size and shape. However, this is not meant to limit the design, and the weave pattern and tightness of the weave of the braided jacket 318 may be altered in any combination such that the perfusion openings 306 are not uniform. Further, changes in the weave pattern and tightness of the weave of the braided jacket 318 may also change the flexibility of the distal shaft 304. For example, and not by way of limitation, the weave pattern of the wire members 338 may be loosened towards the distal portion of the distal shaft 304, thereby increasing the flexibility of the distal portion of the distal shaft 304 and increasing the size of the perfusion openings 306 towards the distal portion of the distal shaft.

In an embodiment, the plurality of wire members 338 of the braided jacket 318 of the distal shaft 304 may include a coating on an outer surface and/or an inner surface thereof. The coating disposed on the outer surface of the plurality of wire members 338 may reduce the surface friction between the distal shaft 304 and the guide catheter or vasculature as the distal shaft 304 is advanced through the vasculature. Additionally, the coating disposed on the inner surface may allow interventional devices to be advanced/retracted more easily within the lumen 324 of the distal shaft 304. The coating is preferably applied to the plurality of wire members 338 prior to weaving the plurality of wire members 338 to form the braided jacket 318. In this manner, the perfusion openings 306 are not blocked by a post-weaving coating. However, a post-weaving coating may be applied provided that the perfusion openings 306 are not blocked by the coating. The coating may be a polymer, such as polyether block amides (e.g. PEBAX®, VESTAMID®), nylon, or any other materials suitable for purposes of the present disclosure. In some embodiments, the coating may be a lubricious coating.

Figure 19:
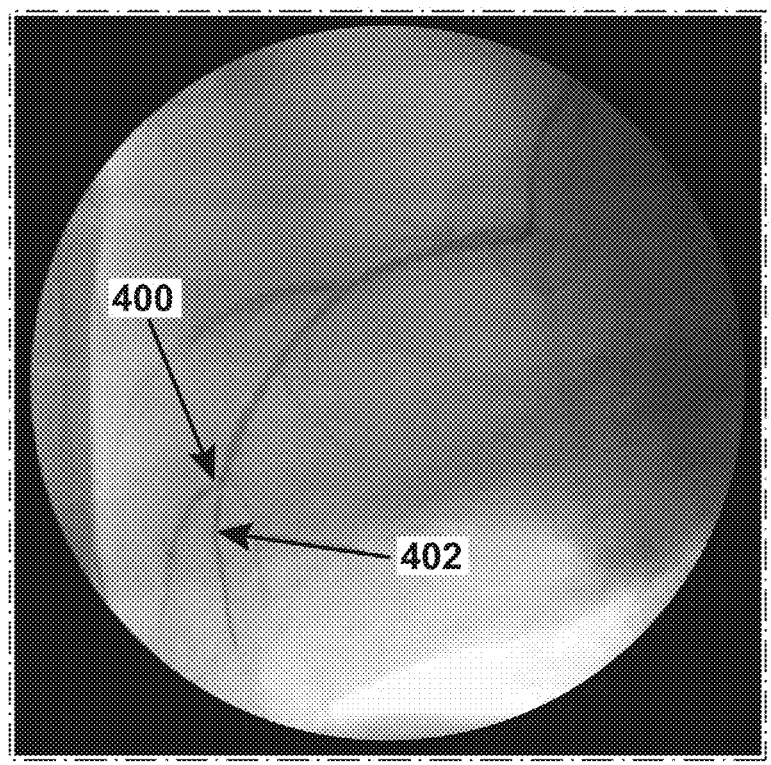
FIG. 19 shows a screen capture of an image of a portion of the vasculature of a swine used in an animal trial.
Figure 20:
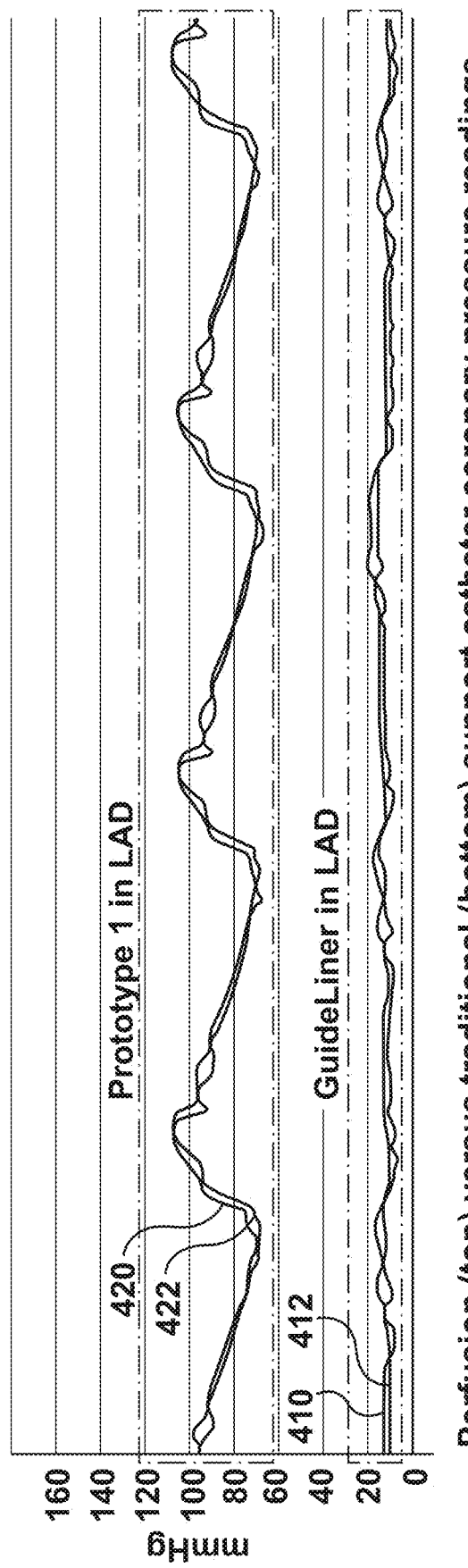
FIG. 20 shows blood pressuring readings taken during an animal trial using a conventional guide extension catheter and using a guide extension catheter with perfusion openings.

As noted in the Background section above, it has been discovered by the inventors hereof that using conventional guide extension catheters without perfusion openings may disrupt blood flow distal of the guide extension catheter. This disruption of blood flow is indicated by a dampened AO pressure reading. This disruption may result in insufficient blood flow to arteries distal of the conventional guide extension catheter. FIGS. 19-20 show results of an animal trial showing how the present invention alleviates the discovered problems with conventional guide extension catheters. In particular, FIG. 19 shows a screen capture of a cine image. FIG. 19 shows a guide extension catheter 400 disposed through a guide catheter, and deep seated into the first diagonal off of the left anterior descending artery (LAD) in a porcine model. A pressure wire 402 (i.e., a guidewire with a pressure sensor at a distal tip thereof, also known as an FFR wire) is extended through the guide extension catheter with the distal tip of the pressure wire extending distal of the distal tip of the guide extension catheter. The pressure wire measures arterial pressure in the vessel distal to the guide extension catheter. An AO pressure sensor measures the pressure at the hub of the guide catheter which is transferred though the column of blood in the guide catheter. The set-up described above with respect to FIG. 19 was done with a conventional guide extension catheter without perfusion openings (GuideLiner® guide extension catheter, Vascular Solutions, Inc.) and with a prototype guide extension catheter including perfusion openings, as described above.

FIG. 20 shows in a single graph the results of the pressure wire and AO pressure readings for the trial using a conventional guide extension catheter without perfusion openings (lines 410, 412) and a guide extension catheter including perfusion openings (lines 420, 422). While these results are shown in a single graph for easy comparison, the test for each was conducted at different times. As can be seen in FIG. 20, the blood pressure readings with the pressure wire and AO pressure sensor (420, 422) when using the perfusion guide extension catheter of the present disclosure are in the normal range for blood pressure readings. When using a conventional guide extension catheter without perfusion openings, the blood pressure readings with both the pressure wire and the AO pressure sensor (410, 412) are dampened. As can be seen, the systolic and diastolic pressures are both under 20 mmHg, and the readings appear closer to a line rather than a wave. In this situation (use of a conventional guide extension catheter), the hemodynamic system was not able to identify the systolic and diastolic portions of the wave because of the dampening. These results show that using a conventional guide extension catheter without perfusion openings causes disruption of the blood flow distal of the guide catheter. Therefore, the AO pressure measurement is dampened due to the disruption of blood flow. Further, these results show that when using a conventional guide extension catheter, insufficient blood flow is reaching arteries distal of guide extension catheter, thereby endangering the patient. These results further show that the use of a guide extension catheter according to the present disclosure (with perfusion holes) dramatically improves blood flow for the AO pressure measurement. Further, the dramatically improved distal pressure measurement shows dramatic improvement in blood flow distal of the inventive guide extension catheter.

While only some embodiments have been described herein, it should be understood that it has been presented by way of illustration and example only, and not limitation. Various changes in form and detail can be made therein without departing from the spirit and scope of the invention, and each feature of the embodiments discussed herein, and of each reference cited herein, can be used in combination with the features of any other embodiment. All patents and publications discussed herein are incorporated by reference herein in their entirety.

What is claimed is:

1. A guide extension catheter, comprising:
a proximal shaft having a first dimension at a distal end;
a distal shaft coupled to the proximal shaft at a transition joint, a proximal portion of the distal shaft having a second dimension greater than the first dimension, and the distal shaft including a jacket and a helical coil structure embedded in the jacket, the distal shaft defining a lumen; and
a plurality of perfusion openings disposed through the jacket between windings of the helical coil structure, the plurality of perfusion openings extending along the distal shaft from a section adjacent the transition joint to a section adjacent a distal end of the distal shaft, wherein the guide extension catheter is configured to extend through a guide catheter such that the guide extension catheter provides additional back support to the guide catheter, and wherein the plurality of perfusion openings are configured to allow fluid communication between an area outside the guide extension catheter and the lumen.

2. The guide extension catheter of claim 1, wherein at least one perfusion opening of the plurality of perfusion openings is circular.

3. The guide extension catheter of claim 1, wherein at least one perfusion opening of the plurality of perfusion openings is oval in shape.

4. The guide extension catheter of claim 1, wherein the length and/or width of each perfusion opening of the plurality of perfusion openings is less than or equal to 0.5 mm.

5. The guide extension catheter of claim 1, wherein a first portion of the plurality of perfusions are disposed through the jacket in a distal portion of the distal shaft, the distal portion comprising the distal end of the distal shaft, and a second portion of the plurality of perfusions are disposed through the jacket in the proximal portion of the distal shaft, the proximal portion comprising a proximal end of the distal shaft.

6. The guide extension catheter of claim 1, wherein some of the plurality of perfusion openings are grouped closely together such that some of the plurality of perfusion openings are more concentrated at a location of the distal shaft than other perfusion openings of the plurality of perfusion openings at other locations along the distal shaft.

7. The guide extension catheter of claim 1, wherein the plurality of perfusion openings of the distal shaft are arranged in a spiral distribution pattern.

8. The guide extension catheter of claim 1, wherein the plurality of perfusion openings are arranged along a common longitudinal axis of the distal shaft.

9. A guide extension catheter, comprising:
a proximal shaft having a first dimension at a distal end;
a distal shaft coupled to the proximal shaft at a transition joint, a proximal portion of the distal shaft having a second dimension greater than the first dimension, and the distal shaft including a jacket and a braided structure embedded in the jacket, the braided structure having a plurality of wire members woven together to form the braided structure, the distal shaft defining a lumen; and
a plurality of perfusion openings disposed through the jacket between wire members of the braided structure, the plurality of perfusion openings extending along the distal shaft from a section adjacent the transition joint to a section adjacent a distal end of the distal shaft,
wherein the guide extension catheter is configured to extend through a guide catheter such that the guide extension catheter provides additional back support to the guide catheter, and
wherein the plurality of profusion openings are configured to allow fluid communication between an area outside the guide extension catheter and the lumen.

10. The guide extension catheter of claim 9, wherein at least one perfusion opening of the plurality of perfusion openings is a circle.

11. The guide extension catheter of claim 9, wherein at least one perfusion opening of the plurality of perfusion openings is oval in shape.

12. The guide extension catheter of claim 9, wherein the length and/or width of each perfusion opening of the plurality of perfusion openings is less than or equal to than 0.5 mm.

13. The guide extension catheter of claim 9, wherein the distal shaft includes more perfusion openings at a distal portion of the distal shaft than at the proximal portion of the distal shaft such that the distal portion of the distal shaft is more flexible than the proximal portion of the distal shaft.

14. The guide extension catheter of claim 9, wherein some of the plurality of perfusion openings are grouped together such that some of the plurality of perfusion openings are more concentrated at a location of the distal shaft than other perfusion openings of the plurality of perfusion openings at other locations along the distal shaft.

15. The guide extension catheter of claim 9, wherein the plurality of perfusion openings of the distal shaft are arranged in a spiral distribution pattern.

16. The guide extension catheter of claim 9, wherein the plurality of perfusion openings of the distal shaft are arranged along a common longitudinal axis of the distal shaft.

17. A guide extension catheter, comprising:
a proximal shaft having a first dimension at a distal end; and
a distal shaft coupled to the proximal shaft at a transition joint, a proximal portion of the distal shaft having a second dimension greater than the first dimension, and the distal shaft including a braided jacket, the braided jacket having a plurality of wire members woven together to form the braided jacket, the distal shaft defining a lumen;
wherein the plurality of wire members are woven together such that a plurality of perfusion openings are formed between the wire members, wherein the plurality of perfusion openings extend from an outer surface of the distal shaft to the lumen of the distal shaft, and wherein perfusion openings of the plurality of perfusion openings are distributed along the distal shaft from a section adjacent the transition joint to a section adjacent a distal end of the distal shaft,
wherein the guide extension catheter is configured to extend through a guide catheter such that the guide extension catheter provides additional back support to the guide catheter, and
wherein the plurality of perfusion openings are configured to allow fluid communication between an area outside the guide extension catheter and the lumen.

18. The guide extension catheter of claim 17, wherein at least one perfusion opening of the plurality of perfusion openings is generally a quadrilateral.

19. The guide extension catheter of claim 17, wherein the length and/or width of each perfusion opening of the plurality of perfusion openings is less than or equal to 0.5 mm.

20. The guide extension catheter of claim 17, wherein the plurality of wire members include a coating, wherein the coating is disposed on the plurality of wire members prior to the wire members being woven.

21. The guide extension catheter of claim 17, wherein the distal shaft further comprises a distal tip at the distal end of the distal shaft.

22. The guide extension catheter of claim 1, wherein the proximal shaft comprises a wire or a hypotube having the first dimension at the distal end.

23. The guide extension catheter of claim 13, wherein the proximal portion of the distal shaft includes the transition joint.

* * * * *